(12) United States Patent
Fukushi et al.

(10) Patent No.: US 11,941,480 B2
(45) Date of Patent: Mar. 26, 2024

(54) INFORMATION PROCESSING SYSTEM, INFORMATION PROCESSING DEVICE, INSOLE, INFORMATION PROCESSING METHOD, AND RECORDING MEDIUM

(71) Applicant: NEC Corporation, Tokyo (JP)

(72) Inventors: Kenichiro Fukushi, Tokyo (JP); Zhenwei Wang, Tokyo (JP); Hiroaki Nakano, Tokyo (JP); Toshinori Takemura, Tokyo (JP); Kentaro Nakahara, Tokyo (JP); Hannah Pokka, Tokyo (JP); Itsumi Kato, Tokyo (JP); Akira Kamei, Tokyo (JP); Chenhui Huang, Tokyo (JP); Hiroshi Kajitani, Tokyo (JP); Koichi Morikawa, Tokyo (JP); Hiroshi Okuda, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/770,472

(22) PCT Filed: Oct. 31, 2019

(86) PCT No.: PCT/JP2019/042810
§ 371 (c)(1),
(2) Date: Apr. 20, 2022

(87) PCT Pub. No.: WO2021/084690
PCT Pub. Date: May 6, 2021

(65) Prior Publication Data
US 2022/0391609 A1    Dec. 8, 2022

(51) Int. Cl.
*G06K 7/14* (2006.01)
*A61B 5/00* (2006.01)
*A61B 5/11* (2006.01)

(52) U.S. Cl.
CPC ............ *G06K 7/1417* (2013.01); *A61B 5/112* (2013.01); *A61B 5/6807* (2013.01)

(58) Field of Classification Search
CPC ..... G06K 7/1417; A61B 5/112; A61B 5/6807; A61B 2562/08
See application file for complete search history.

(56) References Cited

U.S. PATENT DOCUMENTS 9,776,041 B1 * 10/2017 Lachwani ................ A43B 3/34
2007/0043582 A1 * 2/2007 Peveto .................. A43B 23/027
705/26.1

(Continued)

FOREIGN PATENT DOCUMENTS

| JP | 2010-167275 A | 8/2010 |
| JP | 2016-538655 A | 12/2016 |

(Continued)

OTHER PUBLICATIONS

International Search Report for PCT Application No. PCT/JP2019/042810, dated Jan. 28, 2020.

(Continued)

*Primary Examiner* — Matthew Mikels

(57) ABSTRACT

An information processing system includes an identification unit configured to identify unique information on shoes using at least part of a captured image of the shoes, and a setting unit configured to set an association between an acquisition device configured to acquire the unique information and a module device attached to the shoes based on the unique information.

9 Claims, 9 Drawing Sheets

(56) References Cited

U.S. PATENT DOCUMENTS

| | | |
|---|---|---|
| 2014/0336796 A1 | 11/2014 | Agnew |
| 2016/0180440 A1 | 6/2016 | Dibenedetto et al. |
| 2016/0375346 A1 | 12/2016 | Czaja et al. |
| 2017/0308066 A1* | 10/2017 | Farren ..................... A43D 3/02 |
| 2017/0354348 A1 | 12/2017 | Winter |
| 2018/0028861 A1 | 2/2018 | Murakoshi et al. |
| 2018/0166006 A1 | 6/2018 | Cauwood et al. |

FOREIGN PATENT DOCUMENTS

| | | |
|---|---|---|
| JP | 2018-008026 A | 1/2018 |
| JP | 2018-096023 A | 6/2018 |
| WO | 2016/143402 A1 | 9/2016 |

OTHER PUBLICATIONS

JP Office Action for JP Application No. 2021-553989, dated Jul. 25, 2023 with English Translation.

* cited by examiner

| IDENTIFICATION INFORMATION | 11111 | 22222 | 33333 |
|---|---|---|---|
| ADDRESS (LEFT) | AAAA | CCCC | EEEE |
| ADDRESS (RIGHT) | BBBB | DDDD | FFFF |
| TYPE | LEATHER SHOES | PUMPS | SNEAKER |
| SIZE (cm) | 28 | 24.5 | 26.5 |
| GRADIENT (DEGREE) | 1 | 15 | 0 |

INFORMATION PROCESSING SYSTEM, INFORMATION PROCESSING DEVICE, INSOLE, INFORMATION PROCESSING METHOD, AND RECORDING MEDIUM

This application is a National Stage Entry of PCT/JP2019/042810 filed on Oct. 31, 2019, the contents of all of which are incorporated herein by reference, in their entirety.

TECHNICAL FIELD

The present invention relates to an information processing system, an information processing device, an insole, an information processing method, and a recording medium.

BACKGROUND ART

Technologies for acquiring information relating to a person's gait using sensors attached to shoes have been developed.

For example, Patent Document 1 discloses a sensing system configured to estimate a position and a posture of an AR marker using images capturing the AR marker attached to the heel of a shoe. The sensing system is configured to estimate a position vector for each pressure sensor attached onto an insole based on the position and the posture of an AR marker. Subsequently, the sensing system is configured to calculate a ZMP (Zero Moment Point, a center of pressure of floor reaction force) of both feet based on the position vector and the sensing information from pressure sensors.

CITATION LIST

Patent Literature Document

Patent Document 1: International Publication No. WO2016/143402

SUMMARY OF INVENTION

Technical Problem

To acquire information about a person's gait using sensors attached to shoes, it is preferable for a sensing-data-acquiring device to identify shoes equipped with sensors.

An exemplary objective of the present invention is to provide an information processing system, an information processing device, an insole, an information processing method, and a recording medium, which can solve the aforementioned problem.

Solution to Problem

In a first aspect of the present invention, an information processing system includes an identification unit configured to identify unique information on shoes using at least part of a captured image of the shoes, and a setting unit configured to set an association between an acquisition device configured to acquire the unique information and a module device attached to the shoes based on the unique information.

In a second aspect of the present invention, an information processing device includes an identification unit configured to identify unique information on shoes using at least part of a captured image of the shoes, and a setting unit configured to set an association between the information processing device and a module device attached to the shoes based on the unique information.

In a third aspect of the present invention, an insole includes an image representing its own identification information.

In a fourth aspect of the present invention, an information processing method includes the steps of: identifying unique information on shoes using at least part of a captured image of the shoes; and setting an association between an acquisition device configured to acquire the unique information and a module device attached to the shoes based on the unique information.

In a fifth aspect of the present invention, a storage medium is configured to store a program causing a computer to implement the steps of: identifying unique information on shoes using at least part of a captured image of the shoes; and setting an association between an acquisition device configured to acquire the unique information and a module device attached to the shoes based on the unique information.

Advantageous Effects of Invention

According to the information processing system, the information processing device, the insole, the information processing method, and the recording medium described above, it is possible for a sensing-data-acquiring device to identify shoes equipped with sensors.

DESCRIPTION OF EXEMPLARY EMBODIMENTS

Hereinafter, the exemplary non-limiting embodiments of the present invention will be described below, however, the embodiments do not necessarily limit the scope of the invention as defined in the appended claims. In addition, not all the combinations of features described in the embodiments are necessarily essential to solving means.

First Embodiment

Figure 1:
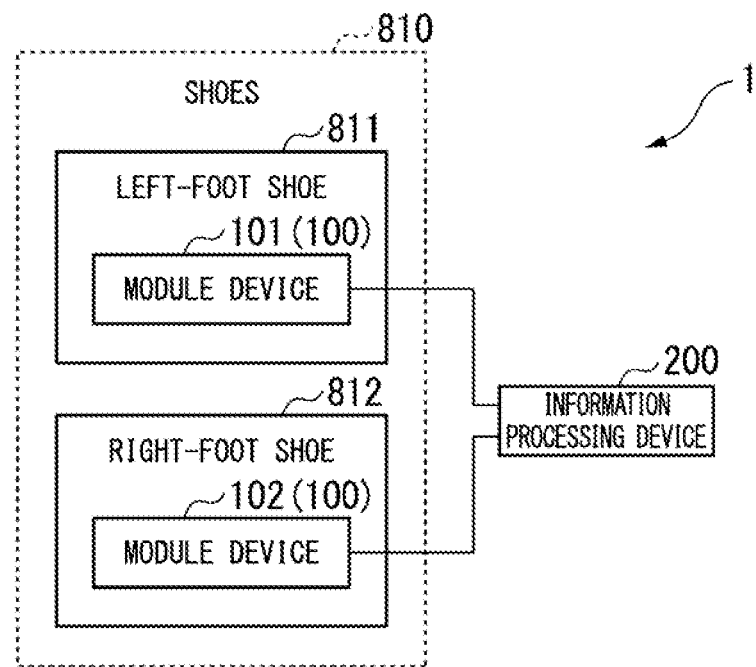
FIG. 1 is a block diagram showing an exemplary device configuration of an information processing system according to the first embodiment.

FIG. 1 is a block diagram showing an exemplary device configuration of an information processing system according to the first embodiment. According to the configuration shown in FIG. 1, an information processing system 1 includes module devices 100 and an information processing device 200.

The information processing system 1 is a system configured to measure and analyze motions of human feet such as a person's gait.

The module devices 100 are attached to shows worn by a person subject to analysis by the information processing system 1. For example, the module device 100 using hexaxial sensors is configured to measure the motion of the module device 100 by measuring triaxial acceleration and triaxial angular velocity of the module device 100.

For example, the module device 100 is configured using a combination of sensors, a microcomputer, and a communication unit.

The motion of the module device 100 to be measured by the module device 100 can be regarded as an equivalent of the motion of a shoe equipped with the module device 100. In addition, the motion of the module device 100 to be measured by the module device 100 can be regarded as an equivalent of the motion of feet of a person subject to analysis by the information processing system 1.

A person subject to analysis by the information processing system 1 will be simply referred to as a target person. In addition, a target person's feet will be simply referred to as feet.

The module devices 100 are attached to shoes, which will be referred to as shoes 810. In a pair of shoes 810, a shoe worn by a left foot will be referred to as a left-foot shoe 811 while a shoe worn by a right foot will be referred to as a right-foot shoe 812.

The following descriptions refer to an exemplary case in which the module devices 100 are attached to the left-foot shoe 811 and the right-foot shoe 812 respectively. In this connection, the module device 100 attached to the left-foot shoe 811 will be referred to as a module device 101. The module device 100 attached to the right-foot shoe 812 will be referred to as a module device 102.

When the information processing system 1 is used to simply measure a foot motion, the module device 100 may be attached to either the left-foot shoe 811 or the right-foot shoe 812.

In addition, the shoes 810 worn by a target person will be referred to as target shoes 810. In this connection, the shoes 810 whose data will be acquired and analyzed by the information processing system 1 may serve as the target shoes 810.

A target person may select and wear any one pair of shoes among multiple pairs of shoes 810. In this case, shoes selected by a target person may serve as the target shoes 810.

The information processing device 200 is configured to acquire measurement data of the module devices 100. For example, the information processing device 200 is configured of a smartphone. The information processing device 200 may be continuously positioned close to the module devices 100 as long as a target person continuously holds the information processing device 200 configured of a portable device such as a smartphone. For this reason, it may be relatively easy for the information processing device 200 to communicate with the module devices 100 via a near-field radio communication between the information processing device 200 and the module devices 100.

In this connection, it is possible to configure the information processing device 200 using other devices than a smartphone such as a personal computer (PC).

The information processing device 200 may analyze measurement data of the module devices 100. For example, the information processing device 200 may calculate a foot trace on a walk using a foot acceleration measured by the module device 100.

The items to be analyzed by the information processing device 200 are not necessarily limited to traces of feet. For example, the information processing device 200 may calculate any one of a number of steps, a moved distance, a consumption of calories due to walking of a target person or any combinations thereof. Alternatively, the information processing device 200 may determine the existence/nonexistence of an abnormality relating to walking of a target person.

The items to be measured by the module devices 100 are not necessarily limited to triaxial velocity and triaxial angular velocity. The module devices 100 should measure any types of data needed for analysis by the information processing device 200.

Figure 2:
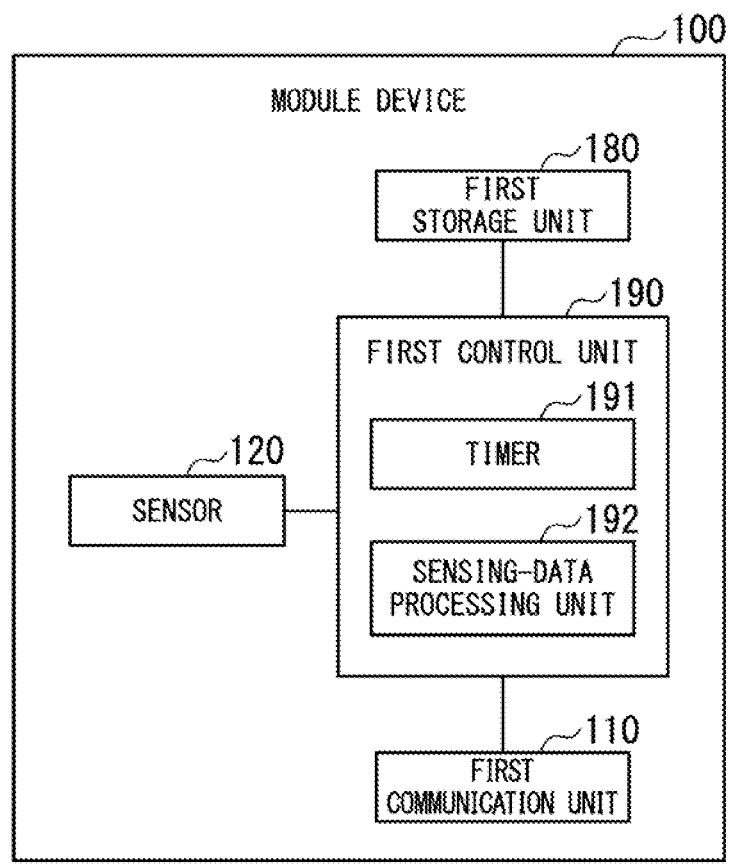
FIG. 2 is a block diagram showing an exemplary functional configuration of a module device according to the first embodiment.

FIG. 2 is a block diagram showing an exemplary functional configuration of the module device 100. In the configuration shown in FIG. 2, the module device 100 includes a first communication unit 110, a sensor 120, a first storage unit 180, and a first control unit 190. The first control unit 190 includes a timer 191 and a sensing-data processing unit 192, The first communication unit 110 is configured to communicate with other devices. For example, the first communication unit 110 communicates with the information processing device 200 to transmit measurement data of the module device 100 to the information processing device 200.

The first communication unit 110 may adopt any communication schemes, which should not be limited to a specific communication scheme. For example, the first communication unit 110 may communicate with the information processing device 200 via a near-field radio communication; but this is not a restriction.

The sensor 120 is configured to measure the motion of the module device 100. For example, the sensor 120 configured of the aforementioned hex-axial sensor may measure the triaxial acceleration and the triaxial angular velocity of the module device 100. As the sensor 120, for example, it is possible to use an IMU (Inertial Measurement Unit).

The first storage unit 180 is configured to store various types of data. The first storage unit 180 may be configured of a storage device installed in the module device 100.

The first control unit 190 is configured to execute various types of processes by controlling various parts of the module device 100. For example, the module device 100 includes a CPU (Central Processing Unit) to read and execute programs from the first storage unit 180, thus achieving the function of the module device 100.

The timer 191 is configured to check the current time using a clock signal. In addition, the timer 191 is configured to switch on/off part of the function of the module device 100 by switching over execution/suspension of a communication function of the first communication unit 110 according to the preset time. By turning off part of the function of the module device 100, it is possible to reduce power consumption of the module device 100, thus relatively increasing an operating time of the module device 100.

In this connection, it is not essential for the timer 191 to switch on/off part of the function of the module device 100. Accordingly, the first control unit 190 may preclude the timer 191 therefrom due to no need to check the current time since it is not necessary to add a time stamp to the communication data of the first communication unit 110.

The sensing-data processing unit 192 carries out processes for measurement data of the sensor 120. For example, the sensing-data processing unit 192 may convert measurement data of the sensor 120 in a data format suited to the communication of the first communication unit 110, and therefore the first communication unit 110 may transmit the converted data therefrom.

Upon setting a calibration for the measurement data of the sensor 120, the sensing-data processing unit 192 may execute the calibration for the measurement data of the sensor 120. When an offset occurs in the measurement data of the sensor 120, for example, the sensing-data processing unit 192 may add a predetermined correction value to or subtract it from the measurement data of the sensor 120, thus cancelling out the offset.

Figure 3:
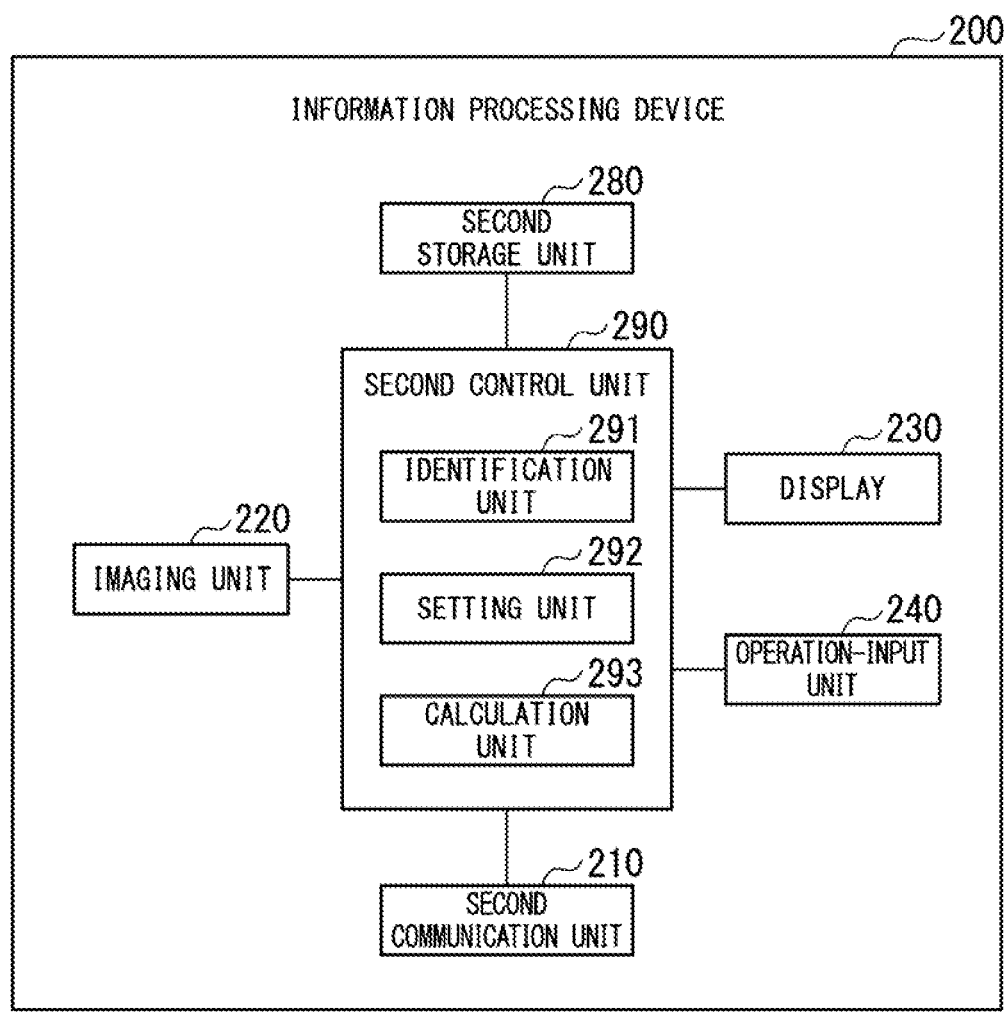
FIG. 3 is a block diagram showing an exemplary functional configuration of an information processing device according to the first embodiment.

FIG. 3 is a block diagram showing an exemplary functional configuration of the information processing device 200. In the configuration shown in FIG. 3, the information processing device 200 includes a second communication unit 210, an imaging unit 220, a display 230, an operation-input unit 240, a second storage unit 280, and a second control unit 290. The second control unit 290 includes an identification unit 291, a setting unit 292, and a calculation unit 293.

The second communication unit 210 is configured to communicate with other devices. For example, the second communication unit 210 communicates with the first communication unit 110 of the module device 100 to receive measurement data (e.g., sensing data of the sensor 120) from the module device 100.

The second communication unit 210 may adopt any communication schemes, which should not be limited to a specific communication scheme as long as the second communication unit 210 can communicate with the first communication unit 110.

The imaging unit 220 configured of a camera or the like is designed to output image data representing captures images. In particular, the imaging unit 220 may capture an image representing at least part of the shoes 810 according to a user operation, thus outputting the captured image.

The captured image of the imaging unit 220 to capture at least part of the shoes 810 is used for the information processing device 200 to identify the target shoes 810.

To identify the shoes 810, the identification information of the shoes 810 having a barcode-format representation such as two-dimensional barcodes may be displayed on the shoes 810.

Figure 4:
FIG. 4 is a top view showing a first example of a shoe having its identification information displayed as a two-dimensional barcode according to the first embodiment.

FIG. 4 shows a first example of the shoe 810 having its identification information to be displayed as a two-dimensional barcode. Specifically, FIG. 4 shows an example of the left-foot shoe 811 in the shoes 810 manufactured as leather shoes.

In an example of FIG. 4, a two-dimensional barcode as the identification information of the shoes 810 is displayed at an imaging-enabled position (e.g., a position viewable from an exterior) on the upper face of an insole of the left-foot shoe 811.

The imaging unit 220 captures the two-dimensional barcode such that the information processing device 200 may read the identification information of the shoes 810 from the two-dimensional barcode, and therefore the information processing device 200 may identify the shoes 810.

The position to display the identification information in the shoes 810 is not necessarily limited to the upper face of an insole but should be placed at a position to capture the image of the identification information of the imaging unit 220. Since the identification information is displayed on the upper face of an insole, it is possible to hide the identification information when a target person wears the shoes 810. This may prevent the aesthetics of the shoes 810 from being damaged by the identification information displayed in the shoes 810.

For example, the module device 100 is provided beneath an insole. For example, a hole adapted to the module device 100 is formed in the body of the shoe(s) 810 under its insole, and therefore the module device 100 can be engaged with and put into the shoe(s) 810. Due to an insole laid inside the shoe(s) 810, it is possible to hide the module device 100 from being viewed from the exterior. Thus, it is possible to prevent the beauty of the shoes 810 from being damaged by the module device 100.

Alternatively, it is possible to form a hole to be engaged with the module device 100 in an insole of the shoe(s) 810 (e.g., the backside of an insole). Accordingly, it is possible to install the module device 100 in the shoe(s) 810 since an insole engaged with the module device 100 is laid inside the shoe(s) 810.

In this connection, the identification information of the shoes 810 may be displayed in either the left-foot shoe 811 or the right-foot shoe 812, alternatively, the identification information of the shoes 810 can be displayed in both the left-foot shoe 811 and the right-foot shoe 812.

When a pair of module devices 100 is attached to a pair of the left-foot shoe 811 and the right-foot shoe 812, for example, a pair of a communication address of the module device 100 for the left-foot shoe 811 and a communication address of the module device 100 for the right-foot shoe 812 can be associated with single identification information. As the identification information, it is possible to display two-dimensional barcodes in the shoes 810.

In this case, the identification information may be displayed in any one of the left-foot shoe 811 and the right-foot shoe 812. Alternatively, the same identification information can be displayed in both the left-foot shoe 811 and the right-foot shoe 812.

Alternatively, a communication address of the module device 100 for the left-foot shoe 811 and a communication address of the module device 100 for the right-foot shoe 812 can be associated with different sets of identification information. In this connection, two-dimensional codes serving as different sets of identification information can be displayed in the left-foot shoe 811 and the right-foot shoe 812 respectively.

As a communication address of the module device 100 associated with the identification information of the shoes 810, it is possible to use various types of communication addresses according to communication schemes adapted to the module device 100. As a communication address of the module device 100, it is possible to use a MAC address (i.e., a Media-Access-Control address) or an IP address (i.e., an Internet-Protocol address); but this is not a restriction.

In this connection, it is possible to use different communication addresses, i.e., a communication address of the module device 100 for the left-foot shoe 811 differently than a communication address of the module device 100 for the right-foot shoe 812. This makes it possible for the information processing device 200 to individually communicate with the module device 100 of the left-foot shoe 811 and the communication device 100 of the right-foot shoe 812.

Figure 5:
FIG. 5 is a top view showing a second example of a shoe having its identification information displayed as a two-dimensional barcode according to the first embodiment.

FIG. 5 is a top view showing a second example of the shoe(s) 810 whose identification information is displayed as a two-dimensional barcode. FIG. 5 shows an example of the left-foot shoe 812 in the shoes 810 as pumps.

In an example of FIG. 5, a two-dimensional barcode as the identification information of the shoe(s) 810 is displayed at an imaging-enabled position on the upper face of an insole laid inside the left-foot shoe 812. Since pumps illustrated in FIG. 5 have a wider opening than leather shoes illustrated in FIG. 4, FIG. 5 shows a two-dimensional barcode displayed on a further front side (or a toe side) than a two-dimensional barcode shown in FIG. 4. However, the position to display a two-dimensional barcode is not necessarily limited to the aforementioned position in FIG. 5 since a two-dimensional barcode should be displayed at an imaging-enabled position.

Figure 6:
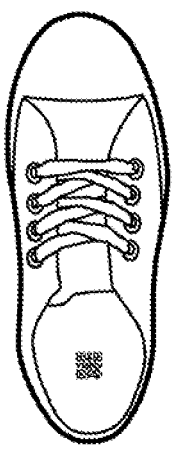
FIG. 6 is a top view showing a third example of a shoe having its identification information displayed as a two-dimensional barcode according to the first embodiment.

FIG. 6 is a top view showing a third example of the shoe(s) 810 whose identification information is displayed as a two-dimensional barcode. FIG. 6 shows an example of the right-foot shoe 812 in the shoes 810 as sneakers.

In an example of FIG. 6, a two-dimensional barcode as the identification information of the shoe(s) 810 is displayed at an imaging-enabled position on the upper face of an insole laid inside the left-foot shoe 812.

When a target person selects and wears any one of three types of shoes 810 as shown in FIGS. 4-6, for example, the target person may capture a two-dimensional barcode displayed in the selected shoe(s) 810 using the information processing device 200. Accordingly, the information processing device 200 can identify the subject shoes 810 by reading the identification information from the captured image of a two-dimensional code.

A method of identifying the target shoes 810 with the information processing device 200 is not necessarily limited to the aforementioned method to use the identification information displayed in the shoes 810.

When the information processing device 200 stores images or feature information about multiple pairs of shoes 810 in advance, for example, the information processing device 200 may identify a captured image of shoes 810 as any one of multiple pairs of shoes 810 via an image-pattern matching using the captured image of the shoes 810.

In this case, the information processing device 200 may identify the shoes 810 using a physical fingerprint representing a surface pattern of the shoes 810 such as flaws formed on the shoes 810.

As described above, it is not necessary to display the identification information in the shoes 810 when the information processing device 200 can identify the shoes 810 via an image-pattern matching of the shoes 810.

The display 230 includes a display screen such as a liquid-crystal panel and an LED (Light-Emitting Diode) panel to display various types of images. For example, the display 230 is configured to display an image captured by the imaging unit 220. In addition, the display 230 is configured to display analysis results produced by analyzing measurement data of the module device(s) 100 with the information processing device 200.

The operation-input unit 240 includes a input device such as touch sensors configuring a touch panel attached to the display screen of the display 230 so as to receive a user operation. For example, the operation-input unit 240 may receive a user operation (or a shutter operation) instructing the imaging unit 220 to capture images.

The second storage unit 280 is configured to store various types of data. For example, the second storage unit 280 may store calculation models used to analyze measurement data of the module device(s) 100. In this connection, calculation models for analyzing measurement data of the module device(s) 100 will be referred to as calculation models relating to the gait of a target person or simply referred to as calculation models.

The second storage unit 280 is configured to store unique information on the shoes 810. Herein, the unique information on the shoes 810 is specified for each pair of shoes 810. The unique information on the shoes 810 includes at least one of the setting information used for communicating with the module devices 100 of the shoes 810 and the information representing characteristics of the shoes 810. In this connection, the second storage unit 280 is configured of a storage device included in the information processing device 200.

Figures 7, 8:
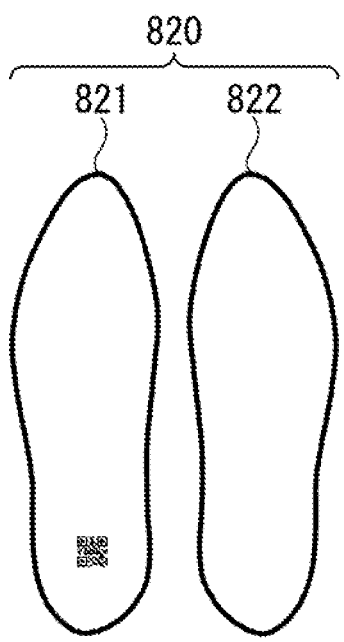
FIG. 7 is a schematic table showing an example of unique information on shoes stored on a second storage unit according to the first embodiment.
FIG. 8 is a pattern diagram showing a pair of insoles having an image of identification information according to the first embodiment.

FIG. 7 is a schematic table showing an example of the unique information on the shoes 810 stored on the second storage device 280. FIG. 7 shows examples of the unique information associated with three pairs of shoes 810 shown in FIGS. 4-6.

In an example of FIG. 7, the unique information on the shoes 810 is shown in a table form, wherein one column shows the unique information for one pair of shoes 810.

In an example of FIG. 7, the unique information on the shoes 810 includes various fields entitled "identification information", "address (left)", "address (right)", "type", "size", and "gradient".

The identification information of the shoes 810 is stored in the "identification information" field. As described above with reference to FIGS. 4-6, for example, the identification information of the shoes 810 may be displayed in the shoes 810 in the form of a two-dimensional barcode. The information processing device 200 reads the identification information of the shoes 810 from the captured image of a two-dimensional barcode and compares the identification information with a plurality of identification information shown in the "identification information" field. Accordingly, the information processing device 200 may identify and read the unique information on the target shoes 810 among a plurality of unique information associated with multiple pairs of shoes 810 stored on the second storage unit 280. Specifically, the information processing device 200 may read the unique information (e.g., one column of information in the example of FIG. 4) whose identification information shown in the "identification information" field which matches the identification information obtained from the captured image among a plurality of unique information associated with multiple pairs of shoes 810 stored on the second storage unit 280.

Alternatively, as described above, the information processing device 200 may perform image-pattern matching with the captured image of the shoes 810 so as to identify the target shoes 810. For this reason, the second storage unit 280 may store an image of the shoes 810, the feature information of the shoes 810, or its combination to be included in the unique information on the shoes 810 in addition to or instead of the identification information, of the shoes 810.

The "address (left)" field stores a communication address of the module device 100 for the left-foot shoe 811 while the "address (right)" field stores a communication address of the module device 100 for the right-foot shoe 812. As communication addresses for the module devices 100, as described above, it is possible to use various types of communication addresses according to communication schemes adapted to the module devices 100.

The "type" field stores the information representing the type of the shoes 810. The example of FIG. 7 shows various types of the shoes 810 such as "leather shoes", "pumps", and "sneakers".

The "size" field stores the information representing the size of the shoes 810. FIG. 7 shows an exemplary case in which the size of the shoes 810 is displayed in units of centimeters (cm). However, the unique information on the shoes 810 may refer to various units of sizes with respect to the shoes 810, which are not necessarily limited to a specific unit of size; hence, it is possible to use arbitrary units of sizes.

The "gradient" field stores the information representing a gradient of the shoes 810 due to heels. In the example of FIG. 7, leather shoes have higher heels than sneakers, while pumps have higher heels than leather shoes. For this reason, the unique information on the shoes 810 indicates the highest gradient of pumps, a next higher gradient of leather shoes, and the lowest gradient of sneakers.

Among various pieces of unique information on the shoes 810 shown in FIG. 7, the information of the "address (left)" field and the information of the "address (right)" field can be regarded as examples of setting information for making communications with the module devices 100 of the shoes 810. The information processing device 200 can conduct communications with the module devices 100 using those pieces of information.

In this connection, the information of the "type" field, the information of the "size" field, and the information of the "gradient" field can be regarded as examples of information representing characteristics of the shoes 810.

When calculation models used for calculation of the gait of a target person differ from each other according to characteristics of the shoes 810, the information processing device 200 may select any one of multiple calculation models according to the information representing characteristics of the shoes 810. In addition, the information processing device 20 may set parameter values for a calculation model according to the information of characteristics of the shoes 810 in addition to or instead of selecting the calculation model.

Alternatively, the second storage unit 280 may store the unique information on the shoes 810 including the identification information of a calculation model to be selected, parameter values to be set to the calculation model, or both the identification information and parameter values.

Alternatively, it is possible to directly display the unique information on the shoes 810 in the shoes 810. For example, it is possible to encode the unique information on the shoes 810 and to display the encoded unique information such as a two-dimensional barcode in the shoes 810. When all pieces of the unique information on the shoes 810 are displayed in the shoes 810, the second storage unit 280 may not necessarily store the unique information on the shoes 810.

For example, it is possible to produce the unique information on the shoes 810 stored on the second storage unit 280 based on the specification information of the shoes 810 or the like.

Alternatively, the information processing device 200 may read part of or the entirety of the unique information on the shoes 810 from the captured image of the shoes 810. For example, it is possible to read from the captured image of the shoes 810 at least one or more items among the type, the size, and the gradient of the shoes 810, thus writing the read item(s) into the unique information stored on the second storage unit 280.

The second control unit 290 is configured to perform various types of processes by controlling various parts of the information processing device 200. For example, a CPU installed in the information processing device 200 may read and execute programs from the second storage device 280 to achieve the function of the second control unit 290.

The identification unit 291 is configured to identify the unique information on the shoes 810 using at least part of an image of the shoes 810 captured by the imaging unit 220.

According to the aforementioned processes, as described above, the identification unit 291 may read the identification information of the shoes 810 from an image of a two-dimensional barcode reflected I the captured image of the shoes 810. Subsequently, the identification unit 291 may read the unique information on the shoes 810 whose identification information matches the identification information of the shoes 810 read from a two-dimensional barcode among a plurality of unique information associated with multiple pairs of shoes 810 stored on the second storage unit 280.

Alternatively, according to the aforementioned processes, it is possible to perform image-pattern matching with the captured image of the shoes 810. Subsequently, the identification unit 291 may read the unique information on the shoes 810 corresponding to the result of image-pattern matching among a plurality of unique information associated with multiple pairs of shoes 810 stored on the second storage unit 280.

According to the aforementioned processes, the identification unit 291 may obtain a physical fingerprint of the shoes 810 from the captures image of the shoes 810. Subsequently, the identification unit 291 may read the unique information corresponding to the physical fingerprint among a plurality of unique information associated with multiple pairs of shoes 810 stored on the second storage unit 280.

In this connection, it is possible to detachably attach insoles to the shoes 810. In this case, the identification unit 291 may identify both the shoes 810 and the insoles attached to the shoes 810. For example, it is possible to display a plurality of identification information on the insoles and the shoes 810.

FIG. 8 is a pattern diagram showing an example of an insole having an image of its identification information. FIG. 8 shows an insole 821 for the left-foot shoe 811 and an insole 822 for the right-foot shoe 812. The insole 821 for the left-foot shoe 821 and the insole 822 for the right-foot shoe 812 will be collectively referred to as insoles 820.

In an example of FIG. 8, a two-dimensional barcode as the identification information of the insoles 810 is displayed on the upper face of the insole 821 for the left-foot shoe 811 at a position close to its heel. Accordingly, when the insoles 820 are laid inside the shoes 810, it is expected to capture a two-dimensional barcode of the insoles 820 which would be visible from the opening of the shoe(s) 810.

It is possible to exchange the insoles 820 among multiple pairs of shoes 810 when the module devices 100 are attached to the insoles 820. By exchanging the insoles 820 among multiple pairs of shoes 810, it is possible to exchange the module devices 100 among multiple pairs of shoes 810.

In this case, a communication address of the module device 100 may be associated with the identification information of the insole 820.

For example, the second storage unit 280 may store a communication address of the module device 100 in association with the identification information of the insole 820. Alternatively, it is possible to encode a communication address of the module device 100 and to display the encoded information as a two-dimensional barcode on the insole 820.

The identification unit 291 is configured to read the identification information of the insole 820 and to acquire a communication address of the module device 100 based on the read identification information.

When the module devices 200 are attached to the insole 821 of the left-foot shoe 811 and the insole 822 of the right-foot shoe 812, as described above in connection with the shoes 810, it is possible to use different communication addresses for the module devices 100.

In this case, as described above in connection with the shoes 810, it is possible to display the identification information of the insoles 820 on any one of or both the insole 821 of the left-foot shoe 811 and the insole 822 of the right-foot shoe 812.

Alternatively, as described above in connection with the shoes 810, it is possible to display different sets of identification information on the insole 821 of the left-foot shoe 811 and the insole 822 of the right-foot shoe 812 respectively.

When the insoles 820 are attached to the shoes 810 in an exchangeable manner, it is possible to display the identification information of the shoes 810 at any position of the shoes 810 other than the insoles 820. For example, it is possible to display a barcode such as a two-dimensional barcode as the identification information of the shoes 810 inside the shoes 810 removing the insoles 820 therefrom at a position similar to the aforementioned positions described in the examples shown in FIGS. 4-6.

By reading the identification information of the shoes 810 and the identification information of the insole 820, the identification unit 291 may identify the shoes 810 and the insoles 820 individually.

Alternatively, as described in the aforementioned processes, the identification unit 291 may identify the shoes 810 via image-pattern matching with the captured image of the shoes 810.

As described above, when the module devices 210 are exchangeable among multiple pairs of shoes 810, the identification unit 291 can identify the shoes 810 equipped with the module devices 100 among multiple pairs of shoes 810.

In this connection, the identification unit 291 may identify the shoes 810 using the identification information of the shoes 810. Alternatively, the identification unit 291 may identify the shoes 810 via image-pattern matching with an image of the shoes 810.

The setting unit 292 is configured to set an association between the information processing device 200 serving as a reading device to read the unique information on the shoes 810 and the module devices 100 attached to the shoes 810 based on the unique information on the shoes 810 which is identified by the identification unit 291.

For example, the setting unit 292 sets a communication connection between the information processing device 200 and the module devices 100 using the communication addresses of the module devices 100 included in the unique information on the shoes 810.

In addition, the setting unit 292 may set a calculation model relating to the gait of a target person based on the unique information on the shoes 810. As described in the aforementioned processes, the setting unit 292 may select any one of calculation models according to the information representing characteristics of the shoes 810. For example, the second storage unit 280 may store various types of calculation models according to various types of shoes such as a calculation model directed to leather shoes, a calculation model directed to pumps, and a calculation model directed to sneakers. Subsequently, the setting unit 292 may select a calculation model according to the type of the target shoes 810.

In addition, the setting unit 292 may set parameter values for a calculation model according to the information representing characteristics of the shoes 810 in addition to or instead of selecting the calculation model.

The setting unit 292 may set an operating time of the module device 100 attached to the shoe(s) 810 based on the unique information on the shoes 810.

When a target person wears leather shoes on weekday commutes while a target person wears sneakers on holidays, for example, the setting unit 292 may set an operating time of the module device 100 attached to sneakers to a holiday mode. The setting unit 292 sets and transmits the operating time to the module device 100 of sneakers via the second communication unit 210. In the module device 100 of sneakers, the timer 191 allows only the part of the function of the module device 100 (e.g., the first communication unit 110 and the sensor 120) to be operated on holidays based on the set operating time.

In addition, the setting unit 292 may set an operating time of the module device 100 of leather shoes to a prescribed time zone which is determined as a time zone of commune. The setting unit 292 sets and transmits the operating time to the module device 100 of leather shoes via the second communication unit 210. In the module device 100 of leather shoes, the timer 191 allows only the part of the function of the module device 100 (e.g., the first communication unit 110 and the sensor 120) to be operated in a time zone of commute on weekdays based on the set operating time.

As described above, it is possible to reduce power consumption of the module device 100 by setting the operating time of the module device 100.

When calculation models used for calculations of the gait of a target person differ from each other according to characteristics of the shoes 810, the information processing device 200 may select any one of calculation models according to the characteristic information of the shoes 810. Alternatively, the information processing device 200 may set parameter values for a calculation model according to the characteristic information of the shoes 810 in addition to or instead of selecting the calculation model.

Alternatively, the second storage unit 280 may store the unique information on the shoes 810 including the identification information of a calculation model to be selected, parameter values to be set to the calculation model, or both the identification information and the parameter values of the calculation model.

The calculation unit 293 is configured to calculate the information relating to the gait of a target person using measurement data of the module device(s) 100. For example, the calculation unit 293 inputs the measurement data of the module device(s) 100 to a calculation model which is selected by the setting unit 292 and whose parameter values are set by the setting unit 292, thus performing calculations according to the calculation model.

Accordingly, the calculation unit 293 produces the information relating to the gait of a target person as an output of the calculation model.

The calculation unit 293 may confirm validity of a calculation model based on calculation results. For example, the calculation unit 293 may compare a calculation result with a predetermined threshold value so as to determine validity of the calculation result. Upon determining an invalidity of the calculation result, the calculation unit 293 may display an alarm message declaring the invalidity of the calculation result on the display 230. Alternatively, the calculation unit 293 may set a valid calculation model again to perform recalculations.

Next, the operation of the information processing device 200 will be described with reference to FIGS. 9-10.

Figure 9:
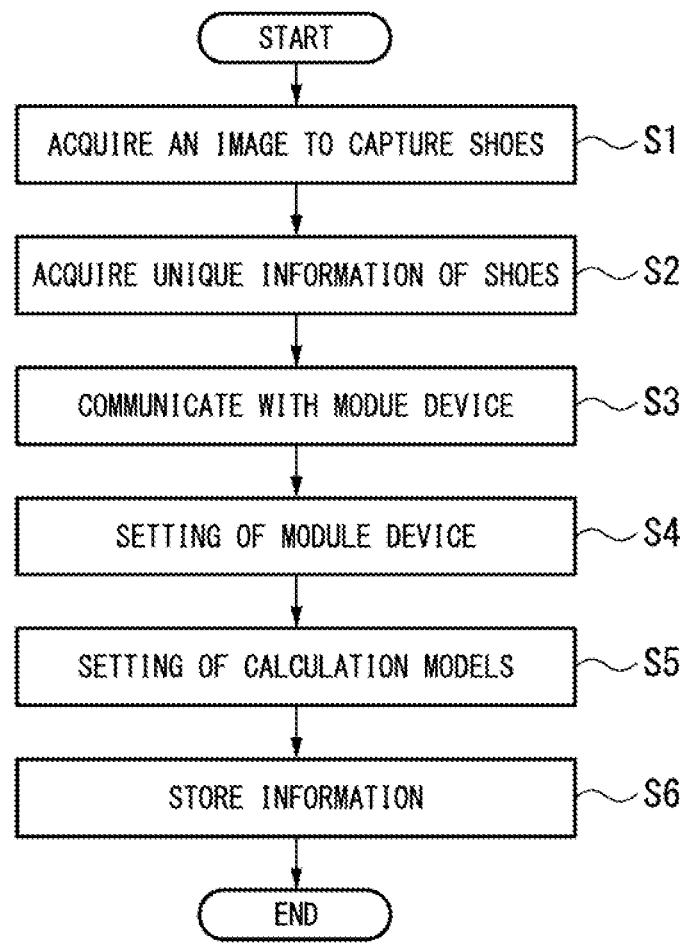
FIG. 9 is a flowchart showing an exemplary procedure of preprocessing to calculate data relating to a gait with the information processing device according to the first embodiment.

FIG. 9 is a flowchart showing an exemplary procedure of preprocessing to calculate data relating to the gait of a target person with the information processing device 200. Assuming a fixed combination of the shoes 810, the module device(s) 100, and the insoles 820, the information processing device 200 needs to perform the process of FIG. 9 once with respect to a pair of shoes 810. In other words, the information processing device 200 does not need to repeat the process of FIG. 9 even when repeatedly calculating data relating to the gait of a target person.

In the process of FIG. 9, the identification unit 291 is configured to acquire a captured image of the target shoes 810 (step S1). Specifically, the imaging unit 220 captures at least part of the target shoes 810 according to a user operation. The identification unit 291 acquires the captured image of the target shoes 810 which is produced by an imaging operation of the imaging unit 220.

Next, the identification unit 291 acquires the unique information on the target shoes 810 (step S2). For example, the identification unit 291 reads the identification information of the target shoes 810 from a barcode reflected in the captured image of the target shoes 810. Subsequently, the identification unit 291 reads from the second storage unit 280 the unique information associated with the identification information. Alternatively, the identification unit 291 may perform image-pattern matching instead of reading the identification information from a barcode with respect to the captured image of the target shoes 810, thus reading the unique information suited to the matching result from the second storage unit 280.

Next, the setting unit 292 communicates with the module device(s) 100 using a communication address of the module device(s) 100 included in the unique information obtained by the identification unit 192 (step S3). Specifically, the setting unit 292 communicates with the module devices 100 attached to the left-foot shoe 811 and the right-foot shoe 812 respectively.

The setting unit 292 sets the module devices 100 (step S4). For example, the setting unit 292 acquires measurement data of the sensor 120 when the module devices 100 suspend its operations, thus calculating an offset occurred in the measurement data. Subsequently, the setting unit 292 makes a setting to the sensing-data processing unit 192 for each module device 100 to perform a calibration for removing the offset from the measurement data. Alternatively, the information processing device 200 may perform a calibration by itself. For example, the setting unit 292 may make a setting of a calibration for the calculation unit 293 instead of the sensing-data processing unit 192.

In addition, the setting unit 292 makes a setting of a calculation model based on the unique information on the shoes 810 (step S5). As described above, the setting unit 292 may select any one of multiple calculation models. In addition, the setting unit 292 may set parameter values for a calculation model in addition to or instead of selecting the calculation model.

Moreover, the setting unit 292 stores its acquired information such as the calibration information and the setting information of a calculation model on the second storage unit 280 (step S6).

After step S6, the information processing device 200 exits the process of FIG. 9.

Figure 10:
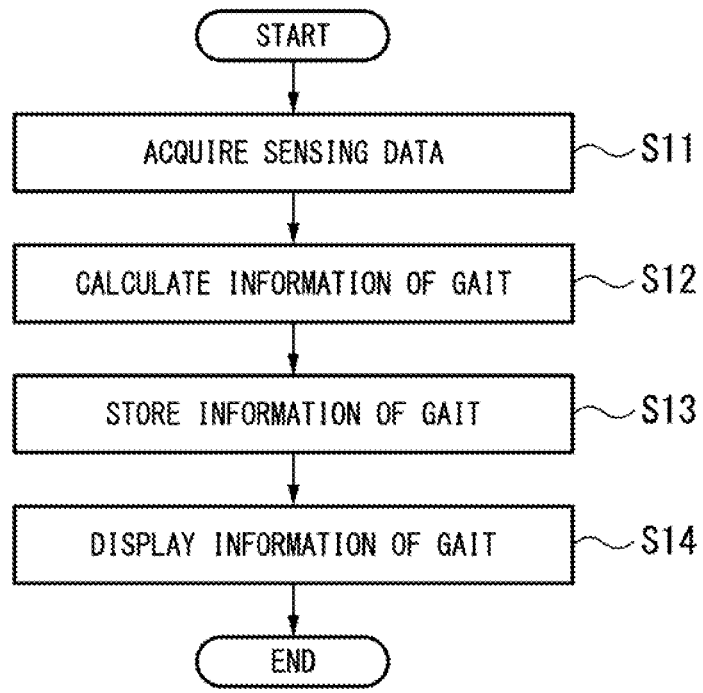
FIG. 10 is a flowchart showing an exemplary procedure of processing to calculate the information relating to a gait with the information processing device according to the first embodiment.

FIG. 10 is a flowchart showing an exemplary procedure to calculate the information relating to the gait of a targe person. For example, the information processing device 200 repeatedly executes the process of FIG. 10 in certain intervals of time within a time zone which is set as a time zone to operate the module devices 100.

In the process of FIG. 10, the calculation unit 293 acquires the measurement data (or sensing data) of the sensor 120 for each module device 100 (step S11).

Next, the calculation unit 293 obtains and inputs the measurement data into a calculation model to calculate the information relating to the gait of a target person (step S12).

Subsequently, the calculation unit 293 produces and stores the information relating to the gait on the second storage unit 280 (step S13).

In addition, the calculation unit 293 controls the display 230 to display the information relating to the gait on the screen (step S14).

After step S14, the information processing device 200 exits the process of FIG. 10.

As described above, the identification unit 292 is configured to identify the unique information on the shoes 810 using at least part of the captured image of the shoes 810. Based on the unique information, the setting unit 292 sets an association between the information processing device 200, serving as an acquisition device to acquire the unique information, and the module devices 100 attached to the shoes 810.

In the information processing system 1, the information processing device 200, serving as a device to acquire sensing data, is able to identify the shoes 810 equipped with the module devices 100 having the sensors 120. By identifying the shoes 810, for example, the information processing device 200 is able to acquire a communication address for each module device 100 attached to the shoes 810 or to set a calculation model relating to the gait according to the characteristics of the shoes 810.

In addition, the setting unit 292 makes a setting of a communication connection between the information processing device 200 and the module device(s) 100 based on the unique information on the shoes 810.

This makes it relatively easy for the information processing device 200 to make a setting of a communication connection with the module device(s) 100. When the unique information on the shoes 810 includes a communication address for each module device 100, for example, the information processing device 200 may automatically establish a communication connection with the module device(s) 100 using the communication address.

The setting unit 292 sets a calculation model relating to the gait of a target person based on the unique information on the shoes 810.

This makes it possible for the information processing device 200 to reflect characteristics of the shoes 810 in a calculation relating to the gait of a target person. In this sense, it is possible for the information processing device 200 to perform a calculation relating to the gait of a target person with relatively high accuracy.

For example, setting unit 292 may set parameter values of a calculation model relating to the gait of a target person based on the unique information on the shoes 810.

This makes it possible for the information processing device 200 to reflect characteristics of the shoes 810 in a calculation relating to the gait of a target person. In this sense, it is possible for the information processing device 200 to perform a calculation relating to the gait of a target person with relatively high accuracy.

The setting unit 292 sets an operating time for each module device 100 based on the unique information on the shoes 810.

Accordingly, it is possible for the information processing system 1 to reduce power consumption of the module device(s) 100, for example, it is possible to increase the time to charge the module device(s) 100 or to continuously use the module device(s) 100 without exchanging its battery to be relatively longer.

The setting unit 291 identifies the unique information on the shoes 810 using a physical fingerprint of the shoes 810 indicated by at least part of the captured image of the shoes 810.

This makes it possible for the information processing device 200 to identify the shoes 810 using the physical fingerprint of the shoes 810. Due to a capacity of the information processing device 200 to identify the shoes 810, for example, it is possible to acquire a communication address for each module device 100 attached to the shoes 810 or to set a calculation model relating to the gait of a target person according to characteristics of the shoes 810.

When the module devices 100 are exchangeable among multiple pairs of shoes 810, the identification unit 291 may identify a specific pair of shoes 810 equipped with the module devices 100 among multiple pairs of shoes 810.

Due to a capacity of the information processing device 200 to identify the shoes 810, for example, it is possible to acquire a communication address for each module device 100 attached to the shoes 810 or to set a calculation model relating to the gait of a target person according to characteristics of the shoes 810.

The insoles 820 have an image showing the identification information of the insoles 820.

For example, the information processing device 200 may identify the insoles 820 using the image so as to acquire the information relating to the identified insoles 820.

Second Embodiment

Part of the function of the information processing device 200 may be executed by another device. The second embodiment refers to an exemplary case in which a server device is configured to implement the function of the calculation unit 293 within the function of the information processing device 200.

Figure 11:
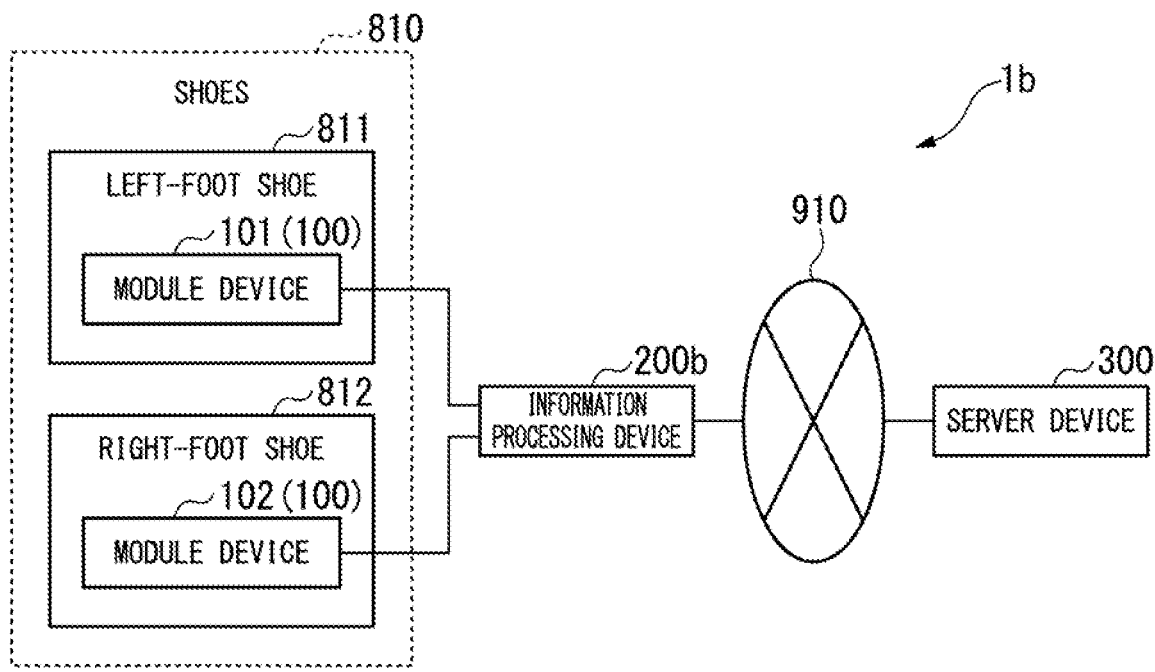
FIG. 11 is a block diagram showing an exemplary device configuration of an information processing system according to the second embodiment.

FIG. 11 is a block diagram showing an exemplary device configuration of an information processing system according to the second embodiment. In the configuration shown in FIG. 11, an information processing system 1b includes the module devices 100, an information processing device 200b, and a server device 300.

The information processing device 200b communicates with the server device 300 through a communication network 910. For example, the communication network 910 may serve as a combination of the Internet and mobile-phone lines; but this is not a restriction. In this connection, mobile-phone networks are wireless communication networks which communication carriers may provide to mobile phones. The communication network 910 may be established externally of the information processing system 1b, or the communication network 910 may serve as part of the information processing system 1b.

Among various parts of FIG. 11, parts similar to the foregoing ones of FIG. 1 will be denoted by the same reference signs (e.g., 100, 101, 102, 810, 811, 812); hence, descriptions thereof will be omitted here.

The information processing system 1b differs from the information processing system 1 in that the function of the information processing device 200 is divided between the information processing device 200b and the server device 300. As to other points, the information processing system 1b is similar to the information processing system 1.

Figure 12:
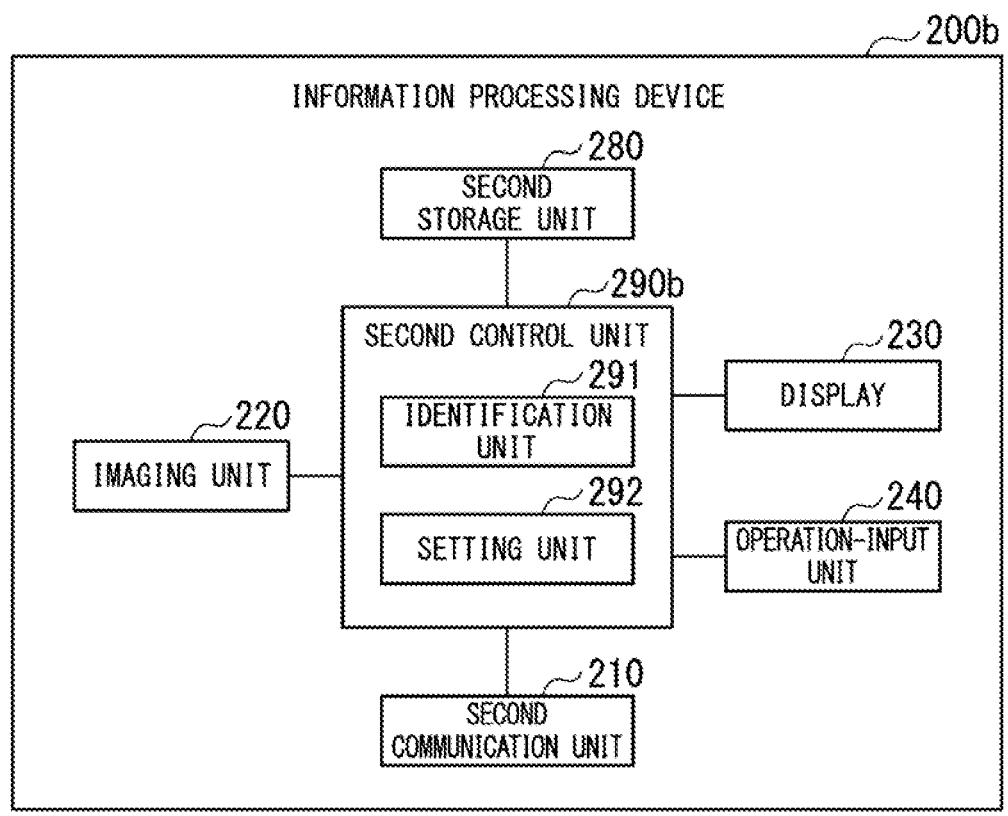
FIG. 12 is a block diagram showing an exemplary functional configuration of an information processing device according to the second embodiment.

FIG. 12 is a block diagram showing an exemplary functional configuration of an information processing deice 200b. In the configuration shown in FIG. 12, the information processing device 200b includes the second communication unit 210, the imaging unit 220, the display 230, the operation-input unit 240, the second storage unit 280, and a second control unit 290b. The second control unit 290b includes the identification unit 291 and the setting unit 292.

As described above, among the function of the information processing device 200 of FIG. 1, the function of the calculation unit 293 is implemented by the server device 300. Therefore, the information processing device 200b differs from the information processing device 200 in that the second control unit 290b precludes the calculation unit 293. As to other points, the information processing device 200b is similar to the information processing device 200.

Figure 13:
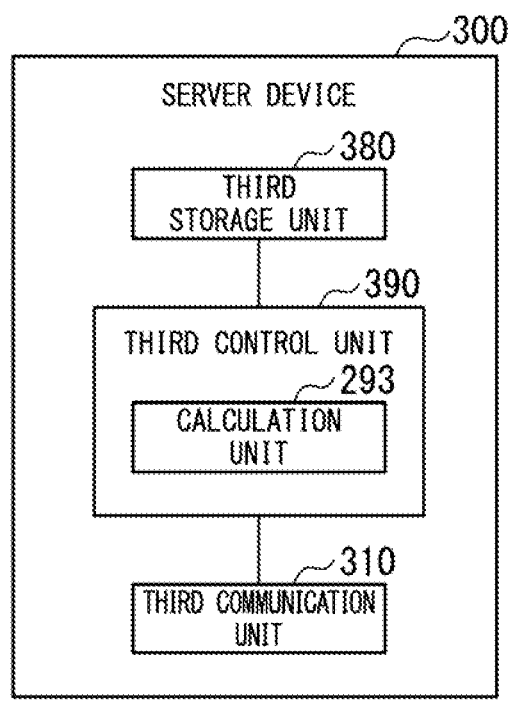
FIG. 13 is a block diagram showing an exemplary functional configuration of a server device according to the second embodiment.

FIG. 13 is a block diagram showing an exemplary functional configuration of the server device 300. In the configuration shown in FIG. 13, the server device 300 includes a third communication unit 310, a third storage unit 380, and a third control unit 390. The third control unit 390 includes the calculation unit 293.

That is, the server device 300 is configured to perform the function of the calculation unit 293 among the function of the information processing device 200 of FIG. 1. For example, the server device 300 is a computer such as a workstation.

The third communication unit 380 is configured to communicate with other devices. In particular, the third communication unit 310 is configured to communicate with the information processing device 200b through the communication network 910.

The third storage device 380 is configured to store various types of data. The third storage device 380 is configured of a storage device included in the server device 300.

The third control unit 390 is configured to perform various types of processes by controlling various parts of the server device 300. In this connection, the server device 300 includes a CPU configured to read and execute programs from the third storage unit 380, thus achieving the function of the third control unit 390.

The calculation unit 293 is similar to the calculation unit 293 of FIG. 1; hence, the same reference sign (i.e., 293) is assigned thereto, thus omitting its description here.

Accordingly, the information processing device 200b needs to bear a relatively small load owing to the server device 300 configured to perform the function of the calculation unit 293. For example, it is possible to perform calculations bearing a relatively large load in real time. When the server device 300 reserves numerous data for serval days or several months, for example, it is possible to feed analysis results of reserved data back to the information processing device 200b.

The server device 300 may perform any one of the identification unit 291 and the setting unit 292 or both of their functions in addition to or instead of the function of the calculation unit 293.

Third Embodiment

Figure 14:
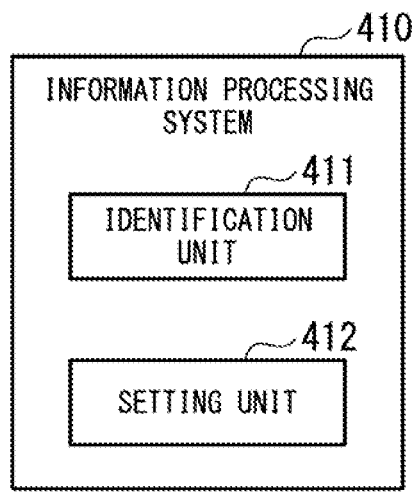
FIG. 14 is a block diagram showing a configuration example of an information processing system according to the third embodiment.

FIG. 14 is a block diagram showing a configuration example of an information processing system according to the third embodiment. An information processing system 410 shown in FIG. 14 includes an identification unit 411 and a setting unit 412.

In this configuration, the identification unit 411 is configured to identify the unique information on shoes using at least part of the captured image of shoes. The setting unit 412 is configured to set an association between an acquisition device configured to acquire the unique information and a module device attached to shoes based on the unique information.

Accordingly, the information processing system 410 allows the device of acquiring the unique information to identify the shoe(s) equipped with the module device. Due to a capacity to identify shoes with the device of acquiring the unique information, for example, it is possible to acquire a communication address of a module device attached to shoes or to set a calculation model relating to the gait of a target person according to characteristics of shoes.

Fourth Embodiment

Figure 15:
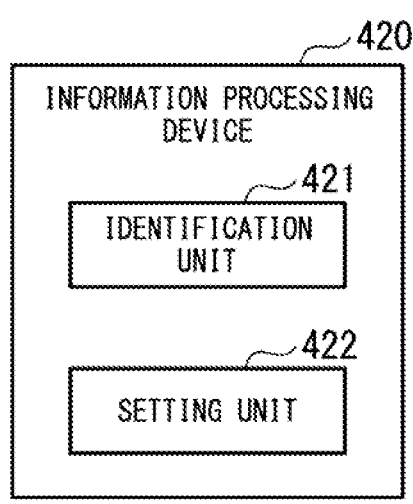
FIG. 15 is a block diagram showing a configuration example of an information processing device according to the fourth embodiment.

FIG. 15 is a block diagram showing a configuration example of an information processing device according to the fourth embodiment. An information processing device 420 shown in FIG. 15 includes an identification unit 421 and a setting unit 422.

In this configuration, the identification unit 421 is configured to identify the unique information on shoes using at least part of the captured image of shoes. The setting unit 422 is configured to set an association between the information processing device 420 and a module device attached to shoes based on the unique information.

Accordingly, the information processing device 420 is able to identify shoes equipped with a module device. Due to a capacity to identify shoes with the device of acquiring the unique information, for example, it is possible to acquire a communication address of a module device attached to shoes or to set a calculation model relating to the gait of a target person according to characteristics of shoes.

Fifth Embodiment

Figure 16:
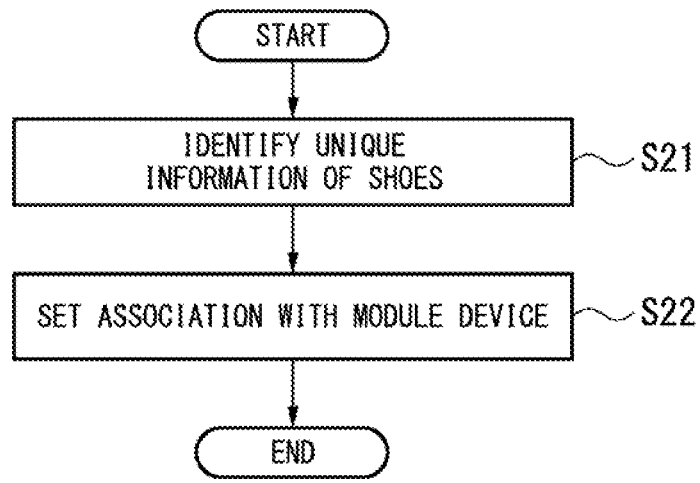
FIG. 16 is a flowchart showing an exemplary procedure of processing in an information processing method according to the fifth embodiment.

FIG. 16 is a flowchart showing an exemplary procedure of processing in an information processing method according to the fifth embodiment.

The process of FIG. 16 includes a step (step S21) for identifying the unique information on shoes using at least part of the captured image of shoes and a step (step S22) for setting an association between an acquisition device configured to acquire the unique information and a module device attached to shoes.

According to the process of FIG. 16, the device for acquiring the unique information is able to identify the shoes equipped with the module device. Due to a capacity to identify the shoes with the device for acquiring the identification information, for example, it is possible to acquire a communication address of the module device attached to the shoes or to set a calculation model relating to the gait of a target person according to characteristics of shoes.

Figure 17:
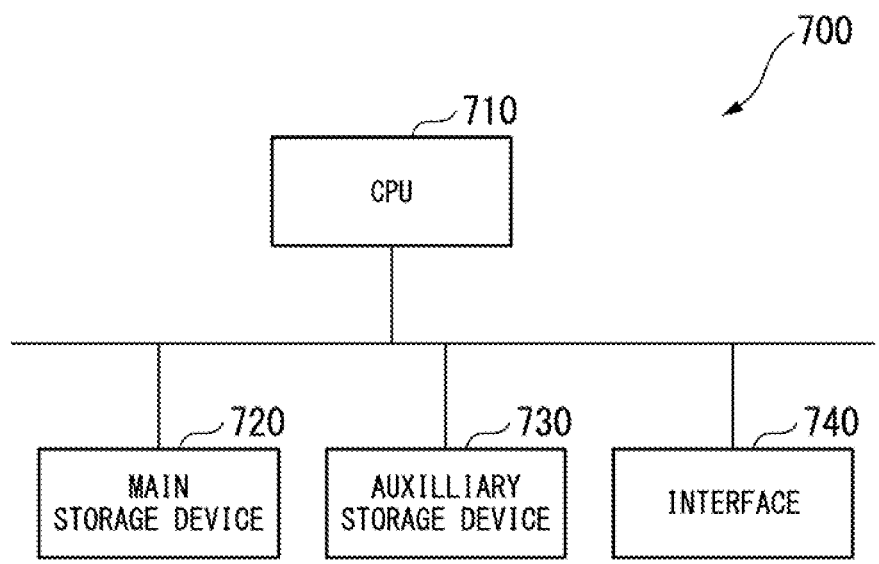
FIG. 17 is a block diagram showing a configuration of a computer according to any one of the foregoing embodiments.

FIG. 17 is a block diagram showing the configuration of a computer according to at least one of the foregoing embodiments.

In the configuration shown in FIG. 17, a computer 700 includes a CPU 710, a main storage device 720, an auxiliary storage device 730, and an interface 740.

At least one or more of the module device 100, the information processing device 200, the information processing device 200b, the server device 300, the information processing system 410, and the information processing device 420, which are described above, may be implemented by the computer 700. In this case, the aforementioned operation for each processing part is realized in the form of programs and stored on the auxiliary storage device 730. The CPU 710 reads programs from the auxiliary storage device 730 so as to unwind programs on the main storage device 720, thus performing the aforementioned processes according to programs. The CPU 710 may secure storage areas corresponding to the aforementioned storage units on the main storage device 720. The interface 740 having a communication function may perform communications between the aforementioned devices and other devices under the control of the CPU 710.

When the module device 100 is implemented by the computer 700, the operation of the first control unit 190 and its internal parts is realized in the form of programs and stored on the auxiliary storage device 730. The CPU 710 reads programs from the auxiliary storage device 730 so as to unwind programs on the main storage device 720, thus performing the aforementioned processes according to programs.

The CPU 710 may secure a storage area corresponding to the first storage unit 180 on the main storage device 720 according to programs. The interface 740 having a communication function performs a communication conducted by the first communication unit 110 under the control of the CPU 170. The interface 740 having its sensor may perform the function of the sensor 120 by acquiring sensing data under the control of the CPU 710.

When the information processing device 200 is implemented by the computer 700, the operation of the second control unit 290 and its internal parts is realized in the form of programs and stored on the auxiliary storage device 730. The CPU 710 reads programs from the auxiliary storage device 730 so as to unwind programs on the main storage device 720, thus performing the aforementioned processes according to programs.

The CPU 710 may secure a storage area corresponding to the second storage unit 280 on the main storage device 720 according to programs.

The interface 740 having a communication function may perform the communication conducted by the second communication unit 210 under the control of the CPU 710. The interface 740 may include an imaging unit configured to perform an imaging operation of the imaging unit 220 under the control of the CPU 710. The interface 740 having its display screen may perform the function of the display 230 by displaying images on the display screen under the control of the CPU 710. The interface 740 may include an input device configured to receive a user operation, thus performing the function of the operation-input unit 240.

When the information processing device 200b is implemented by the computer 700, the operation of the second control unit 290b and its internal parts is realized in the form of programs and stored on the auxiliary storage device 730. The CPU 710 reads programs from the auxiliary storage device 730 so as to unwind programs on the main storage device 720, thus achieving the aforementioned processes according to programs.

The CPU 710 may secure a storage area corresponding to the second storage unit 280 on the main storage device 720 according to programs.

The interface 740 having a communication function may perform a communication conducted by the second communication unit 210 under the control of the CPU 710. The interface 740 may include an imaging unit configured to perform an imaging operation of the imaging unit 220 under the control of the CPU 710. The interface 740 having its display screen may preform the function of the display 230 by displaying images on the display screen under the control of the CPU 710. The interface 740 may include an input device configured to receive a user operation so as to perform the operation of the operation-input unit 240.

When the server device 300 is implemented by the computer 700, the operation of the third control unit 390 and its internal parts is realized in the form of programs and stored on the auxiliary storage device 730. The CPU 710 reads programs from the auxiliary storage device 730 so as to unwind programs on the main storage device 720, thus performing the aforementioned processes according to programs.

The CPU 710 may secure a storage area corresponding to the third storage unit 380 on the main storage device 720 according to programs. The interface 740 having a communication function may perform a communication conducted by the third communication unit 310 under the control of the CPU 710.

When the information processing system 410 is implemented by the computer 700, the operations of the identification unit 411 and the setting unit 412 are realized in the form of programs and stored on the auxiliary storage device 730. The CPU 710 reads programs from the auxiliary storage device 730 so as to unwind programs on the main storage device 720, thus performing the aforementioned processes according to programs.

When the information processing device 420 is implemented by the computer 700, the operations of the identification unit 421 and the setting unit 422 are realized in the form of programs and stored on the auxiliary storage unit 730. The CPU 710 reads programs from the auxiliary storage device 730 so as to unwind programs on the main storage device 720, thus performing the aforementioned processes according to programs.

In this connection, it is possible to store programs achieving part of or the entirety of the functions realized by the module device 100, the information processing device 200, the information processing device 200b, and the server device 300 on computer-readable storage media; hence, a computer system may achieve the aforementioned processes by loading programs stored on storage media and executing programs. Herein, the term "computer system" may include an OS (Operating System) and hardware such as peripheral devices.

The term "computer-readable storage media" refer to flexible disks, magneto-optical disks, ROM, portable media such as CD-ROM, storage devices such as hard disks embedded in computer systems, or the like. The aforementioned programs may achieve part of the foregoing functions or may be combined with pre-stored programs of computer systems to achieve the foregoing functions.

Heretofore, the exemplary non-limiting embodiments of the present invention have been described in detail with reference to the accompanying drawings, however, concrete configurations are not necessarily limited to the foregoing embodiments; hence, the present invention may include any design changes without departing from the subject matter of the invention.

In this connection, part of or the entirety of the foregoing embodiments can be defined as the following appendixes, however, which are not restrictive.

APPENDIX 1

An information processing system includes an identification unit configured to identify unique information on shoes using at least part of a captured image of the shoes, and a setting unit configured to set an association between an acquisition device configured to acquire the unique information and a module device attached to the shoes based on the unique information.

APPENDIX 2

In the information processing system according to appendix 1, the setting unit is configured to set a communication connection between the acquisition device and the module device based on the unique information.

APPENDIX 3

In the information processing system according to appendix 1 or appendix 2, the setting unit is configured to set a calculation model relating to the gait of a person wearing the shoes based on the unique information.

APPENDIX 4

In the information processing system according to appendix 3, the setting unit is configured to set a parameter value to the calculation model based on the unique information.

APPENDIX 5

In the information processing system according to any one of appendix 1 through appendix 4, the setting unit is configured to set an operating time of the module device based on the unique information.

APPENDIX 6

In the information processing system according to any one of appendix 1 through appendix 5, the identification unit is configured to identify the unique information on the shoes using a physical fingerprint of the shoes indicated by the captured image.

APPENDIX 7

In the information processing system according to any one of appendix 1 through appendix 6, when the module device is exchangeable among multiple pairs of shoes, the identification unit is configured to identify the shoes equipped with the module device among multiple pairs of shoes.

APPENDIX 8

An information processing device includes an identification unit configured to identify unique information on shoes using at least part of a captured image of the shoes, and a setting unit configured to set an association between the information processing device and a module device attached to the shoes based on the unique information.

APPENDIX 9

An insole includes an image representing its own identification information.

APPENDIX 10

An information processing method includes the steps of: identifying unique information on shoes using at least part of a captured image of the shoes; and setting an association between an acquisition device configured to acquire the unique information and a module device attached to the shoes based on the unique information.

APPENDIX 11

A computer-readable storage medium stores a program causing a computer to implement the steps of: identifying unique information on shoes using at least part of a captured image of the shoes; and setting an association between an acquisition device configured to acquire the unique information and a module device attached to the shoes based on the unique information.

INDUSTRIAL APPLICABILITY

The exemplary non-limiting embodiments of the present invention are applicable to information processing systems, information processing devices, insoles, information processing methods, and recording media.

REFERENCE SIGNS LIST 1, 1b, 410 information processing system
100 module device
110 first communication unit
120 sensor
180 first storage unit
190 first control unit
191 timer
192 sensing-data processing unit
200, 200b, 420 information processing device
210 second communication unit
220 imaging unit
230 display
240 operation-input unit
280 second storage unit
290, 290b second control unit
291, 411, 421 identification unit
292, 412, 422 setting unit
293 calculation unit
300 server device
310 third communication unit
380 third storage unit
390 third control unit

What is claimed is:

1. An information processing system comprising:
a processor; and
a storage storing a program a executable by the processor to:
identify unique information on shoes using at least part of a captured image of the shoes; and
set an association between an acquisition device configured to acquire the unique information and a module device attached to the shoes based on the unique information,
wherein the unique information on the shoes includes identification information of the shoes, a type of the shoes, a size of the shoes, and a gradient of the shoes.

2. The information processing system according to claim 1, wherein the program is executable by the processor to further set a communication connection between the acquisition device and the module device based on the unique information.

3. The information processing system according to claim 1, wherein the program is executable by the processor to further set a calculation model relating to a gait of a person wearing the shoes based on the unique information.

4. The information processing system according to claim 3, wherein the program is executable by the processor to further set a parameter value to the calculation model based on the unique information.

5. The information processing system according to claim 1, wherein the program is executable by the processor to further set an operating time of the module device based on the unique information.

6. The information processing system according to claim 1, wherein the program is executable by the processor to further identify the unique information on the shoes using a physical fingerprint of the shoes indicated by the captured image.

7. An information processing device comprising:
a processor; and
a storage storing a program a executable by the processor to:
identify unique information on shoes using at least part of a captured image of the shoes; and
set an association between the information processing device and a module device attached to the shoes based on the unique information,
wherein the unique information on the shoes includes identification information of the shoes, a type of the shoes, a size of the shoes, and a gradient of the shoes.

8. An information processing method comprising:
identifying, by a processor, unique information on shoes using at least part of a captured image of the shoes; and
setting, by a processor, an association between an acquisition device configured to acquire the unique information and a module device attached to the shoes based on the unique information, wherein the unique information on the shoes includes identification information of the shoes, a type of the shoes, a size of the shoes, and a gradient of the shoes.

9. A non-transitory computer-readable storage medium storing a program executable by a computer to:
   identify unique information on shoes using at least part of a captured image of the shoes; and
   set an association between an acquisition device configured to acquire the unique information and a module device attached to the shoes based on the unique information,
   wherein the unique information on the shoes includes identification information of the shoes, a type of the shoes, a size of the shoes, and a gradient of the shoes.

* * * * *